United States Patent [19]

Cogburn

[11] Patent Number: 4,929,600
[45] Date of Patent: May 29, 1990

[54] ENDOCRINE MANIPULATION TO IMPROVE BODY COMPOSITION OF POULTRY

[75] Inventor: Larry A. Cogburn, New London, Pa.

[73] Assignee: University of Deleware, Newark, Del.

[21] Appl. No.: 169,737

[22] Filed: Mar. 18, 1988

[51] Int. Cl.$^5$ .................. A61K 37/36; A61K 35/55; A61K 31/195
[52] U.S. Cl. ........................................ 514/2; 514/21; 514/567
[58] Field of Search ................... 514/2, 5, 12, 21, 567; 424/85, 111; 530/308

[56] References Cited

U.S. PATENT DOCUMENTS

| | | | |
|---|---|---|---|
| 2,591,107 | 1/1952 | Turner et al. | 514/5 |
| 4,407,819 | 10/1983 | Kiernan et al. | |
| 4,493,828 | 1/1985 | Leung et al. | 514/19 |
| 4,562,175 | 12/1985 | Chang et al. | |
| 4,562,197 | 12/1985 | Snarey et al. | |
| 4,599,229 | 7/1986 | Maccecchini | 424/85 |
| 4,675,189 | 6/1987 | Kent et al. | |
| 4,686,098 | 8/1987 | Kopchick et al. | |
| 4,818,531 | 4/1989 | Anderson et al. | 424/111 |

FOREIGN PATENT DOCUMENTS

| | | | |
|---|---|---|---|
| 0085036 | 8/1983 | European Pat. Off. | 514/2 |
| 0177819 | 4/1986 | European Pat. Off. | 514/12 |
| 0192360 | 8/1986 | European Pat. Off. | 514/2 |

OTHER PUBLICATIONS

Thorpe, P. E. and W. Ross, "The Preparation and Cytoxic Properties of Antibody–Toxin Conjugates" *Immunological Reviews* 62, 1982, p. 121.
Stewart et al., "Variation in Growth Hormone, Triiodothyronine ($T_3$) and Lipogenic Enzyme Activity in Broiler Strains Differing in Growth and Fatness" *Growth*, 47(4), 411–25, 1983; CA100(21): 171797.
C. P. Alfonso and L. A. Cogburn, Hepatic Thyroxine 5'–Monodeiodinase (5'–MDI) Activity in Broiler Chickens Fed Thyroid Active Substances, *Poultry Sci.* 65(Suppl.1):4 1986).
P. C. Allen and J. P. McMurtry, Changes in Pancreatic Hormones Associated with Coccidiosis, *Poultry Sci.* 63:1128–1135 (1984).
P. K. Baker et al., Use of a β-Adrenergic Agonist to Alter Muscle and Fat Deposition in Lambs, *J. Anim. Sci.* 59:1256–1261 (1984).
D. E. Bauman et al., Responses of High–Producing Dairy Cows to Long–Term Treatment with Pituitary Comatotropin and Recombinant Somatotropin, *J. Dairy Sci.* 68:1352–1362 (1985).
D. H. Beerman et al., Effects of Cimaterol and Fishmeal on Performance, Carcass Characteristics and Skeletal Muscle Growth in Lambs, *J. Anim. Sci.* 62:370–380 (1986).
P. Bohlen et al., Isolation and Characterization of the Porcine Hypothalamic Growth Hormone Releasing Factor, *Biochem. Biophys. Res. Comm.* 116:726–734 (1983).
M. B. Bolger et al., Molecular Interactions between Thyroid Hormone Analogs and the Rat Liver Nuclear Receptor, *J. Biol. Chem.* 255:10271–10278 (1980).
S. J. Bowen et al., Influence of Triiodothyronine and Growth Hormone on Growth of Dwarf and Normal Chickens: Interactions of Hormones and Genotype, *Comp. Biochem. Physiol.* 86A:137–142 (1987).
R. Brazeau et al., Growth Hormone–Releasing Factor from Ovine and Caprine Hypothalamus: Isolation, Sequence Analysis and Total Synthesis, *Biochem. Biophys. Res. Comm.* 125:606–614 (1984).
F. C. Buonomo and C. A. Baile, Effect of Daily Injections of Growth Hormone–Releasing Factor and (List continued on next page.)

*Primary Examiner*—Jacqueline M. Stone
*Assistant Examiner*—Jean Witz

[57] ABSTRACT

The body composition of poultry is improved by a hormonal strategy that involves either:

(1). increasing plasma levels of thyroid hormone by about 2- to 3-fold during the finishing phase (e.g., for chickens, 3 to 6 or 7 weeks-of-age) by providing feed containing 0.1 to 1 ppm of metabolically-active thyroid hormone of the formula:

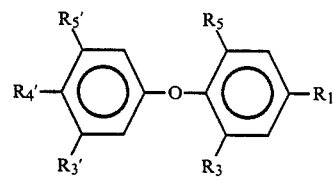

wherein R1 is the residue of a carboxylic acid such as an alpha-amino acid or an aliphatic carboxylic acid, e.g. L-alanine, D-alanine, acetic acid, or propionic acid
R3 is iodine (I)
R5 is iodine (I) or hydrogen (H)
R3' is iodine (I) or the residue of an aliphatic carboxylic acid such as butyric acid, or propionic acid
R5' is iodine (I) or hydrogen (H)
R4' is hydroxy (OH)

(2). increasing plasma levels of metabolically-active thyroid hormone by 2- to 3-fold and increasing plasma levels of growth hormone or glucagon by 2- to 10-fold for 15 to 30% of each day with any suitable method during the finishing phase of poultry growth.

Marked depletion of body fat and increased body protein content are obtained with minimal loss of growth rate or efficiency of feed conversion.

16 Claims, No Drawings

OTHER PUBLICATIONS

Thyrotropin-Releasing Hormone on Growth and Endocrine Parameters in Chickens, *Dom. Anim. Endocrinol.* 4:269-276 (1986).

F. C. Buonomo and C. A. Baile, Recombinant Bovine Somatotropin Stimulates Short Term Increases in Growth Rate and Insulin-Like Growth Factor 1 (IGF-I) in Chickens, *Dom. Anim. Endocrinol.* 5:219-229 (1988).

F. C. Buonomo et al., Effects of Somatostatin Immunoneutralization on Growth and Endocrine Parameters in Chickens, *Dom. Anim. Endocrinol.* 4:191-200 (1987).

W. H. Burke et al., The Properties of Recombinant Chicken Growth Hormone and its Effects on Growth, Body Composition, Feed Efficiency, and Other Factors in Broiler Chickens, *Endocrinology* 120:651-658 (1987).

R. G. Campbell et al., Interrelationships Between Energy Intake and Endogenous Porcine Growth Hormone Administration on the Performance, Body Composition and Protein and Energy Metabolism of Growing Pigs Weighing 25 to 55 Kilograms Live Weight, *J. Anim. Sci.* 66:1643-1655 (1988).

L. A. Cogburn and R. M. Freeman, Response Surface on Daily Thyroid Hormone Rhythms in Young Chickens Exposed to Constant Ambient Temperature, *Gen. Comp. Endocrinol.* 68:113-123 (1987).

L. A. Cogburn et al., Growth, Metabolic and Endocrine Responses of Broiler Cockerels Given a Daily Subcutaneous Injection of Natural or Biosynthetic Chicken Growth Hormone, *J. Nutr.* (accepted) (1989).

V. Coiro et al., Effect of Hypothyroidism and Thyroxine Replacement on Growth Hormone in the Rat, *Endocrinology* 105:641-646 (1979).

R. H. Dalrymple et al., A Repartitioning Agent to Improve Performance and Carcass Composition of Broilers, *Poultry Sci.* 63:2376-2383 (1984).

Decuypere et al., Effects of Hyper- or Hypothyroid Status on Growth, Adiposity and Levels of Growth Hormone, Somatomedin C and Thyroid Metabolism in Broiler Chickens, *Reprod. Nutr. Develop.* 27:555-565 (1987).

F. Esch et al., Isolation and Characterization of the Bovine Hypothalamic Growth Hormone Releasing Factor, *Biochem. Biophys. Res. Comm.* 117:772-779 (1983).

T. D. Etherton et al., Stimulation of Pig Growth Performance by Porcine Growth Hormone: Determination of the Dose-Response Relationship, *J. Anim. Sci.* 64:433-443 (1987).

R. E. Hammer et al., Expression of Human Growth Hormone-Releasing Factor in Transgenic Mice Results in Increased Somatic Growth, *Nature* 315:413-416 (1985a).

R. E. Hammer et al., Production of Transgenic Rabbits, Sheep and Pigs by Microinjection, *Nature* 315:680-683 (1985b).

S. Harvey, J., Thyroid Hormones Inhibit Growth Hormone Secretion in Domestic Fowl, *Endocrinol.* 96:329-334 (1983).

S. Harvey and S. C. Scanes, Purification and Radioimmunoassay of Chicken Growth Hormone, *J. Endocrinol.* 73:321-329 (1977).

R. L. Hazelwood, Pancreatic Hormones, Insulin/-Glucagon Molar Ratios, and Somatostatin as Determinants of Avian Carbohydrate Metabolism, *J. Exp. Zool.* 232:647-652 (1984).

R. L. Hazelwood, Peripheral Endocrine Secretions and Carbohydrate Metabolism, in *Avian Physiology* (P. D. Sturkie ed.) Springer-Verlag, pp. 303-325 (1986).

Hervas et al., Rapid Effects of Single Small Doses of L-Thyroxine and Triiodo-L-Thyronine on Growth Hormone, as Studied in the Rat by Radioimmunoassay, *Endocrinology* 97:91-101 (1975).

F. C. Leung et al., Thyrotropin-Releasing Hormone Stimulates Body Weight Gain and Increases Thyroid Hormones and Growth Hormone in Plasma of Cockerels, *Endocrinology* 115:736-740 (1984).

F. C. Leung et al., Effects on Dietary Thyroid Hormones on Growth and Serum $T_3$, $T_4$, and Growth Hormone in Sex-Linked Dwarf Chickens, *Proc. Soc. Exp. Biol. Med.* 177:77-81 (1984).

F. C. Leung et al., Effects on Dietary Thyroid Hormones on Growth, Plasma $T_3$ and $T_4$ and Growth Hormone in Normal and Hypothyroid Chickens, *Gen. Comp. Endocrinol.* 59:91-99 (1985).

F. C. Leung et al., Purified Chicken Growth Hormone (GH) and a Human Pancreatic GH-Releasing Hormone Increase Body Weight Gain in Chickens, *Endocrinology* 118:1961-1965 (1986).

S. S. Liou et al., Plasma Hormone Responses of Broiler Chickens Given Daily Injections of Growth Hormone or Fed Thyroid-Active Hormones, *Poultry Sci.* 64(Suppl.1):136 (1985) (Abstract).

J. A. Marsh et al., Enhanced Growth and Immune Development in Dwarf Chickens Treated with Mammalian Growth Hormone and Thyroxine, *Proc. Soc. Exp. Biol. Med.* 175:351-360 (1984).

J. A. Marsh et al., Effects of Triiodothyronine Treatments on Body and Organ Growth and the Development of Immune Function in Dwarf Chickens, *Proc. Soc. Exp. Biol. Med.* 177:82-91 (1984).

J. D. May, Effect of Dietary Thyroid Hormone on Growth and Feed Efficiency of Broilers, *Poultry Sci.* 59:888-892 (1980).

J. D. May, Effect of Dietary Thyroid Hormones on Serum Hormone Concentration, Growth, and Body Composition of Chickens, *Aspects of Avian ... Implications*, (C. G. Scanes et al., eds.) Tex. Tech. Univ. Press 26:185-189 (1982).

R. D. Palmiter et al., Dramatic Growth of Mice that Develop from Eggs Microinjected with Metallothionein-Growth Hormone Fusion Genes, *Nature* 300:611-615 (1982).

R. D. Palmiter et al., Metallothionein-Human GH Fusion Genes Stimulate Growth of Mice, *Science* 222:809-814 (1983).

J. P. Peters, Consequences of Accelerated Gain and Growth Hormone Administration for Lipid Metabolism in Growing Beef Steers, *J. Nutr.* 116:2490-2503 (1986).

J. A. Proudman, Recombinant-Derived Chicken (List continued on next page.)

OTHER PUBLICATIONS

Growth Hormone Used for Radioimmunoassay, *Proc. Soc. Exp. Biol. Med.* 175:417–419 (1984).

K. L. Raheja et al., Elevated Insulin/Glucagon Ratios and Decreased Cyclic AMP Levels Accompany the Glycogen and Triglyceride Storage Syndrome in the Hypothyroid Chick, *Horm. Metab. Res.* 12:51–55 (1980).

C. G. Scanes, et al., Abnormalities in the Plasma Concentrations of Thyroxine, Tri-iodothyronine and Growth Hormone in Sex-Linked Dwarf and Autosomal Dwarf White Leghorn Domestic Fowl (*Gallus domesticus*), *J. Endocrinol.* 97:127–135 (1983).

C. G. Scanes et al., Synthetic Human Pancreatic Growth Hormone Releasing Factor (GRF) Stimulates Growth Hormone Secretion in the Domestic Fowl (*Gallus domesticus*), *Life Sci.* 34:1127–1134 (1984).

C. G. Scanes et al., Effect of Chicken Growth Hormone Triiodothyronine and Hypophysectomy in Growing Domestic Fowl, *Growth* 50:12–31 (1986).

C. G. Scanes et al., Stimulation of in-vivo Growth Hormone Secretion in Young Chickens by Rat Hypothalamic Growth Hormone-Releasing Factor and Synthetic Analogues, *J. Endocrinol.* 108:412–416 (1986).

G. S. G. Spencer et al., the Effect of Immunization Against Somatostatin on Growth Rates and Growth Hormone Secretion in the Chicken, *Comp. Biochem. Physiol.* 85A:553–556 (1986).

J. Spiess et al., Characterization of Rat Hypothalamic Growth Hormone-Releasing Factor, *Nature* 303:532–535 (1983).

L. M. Souza et al., Application of Recombination DNA Technologies to Studies on Chicken Growth Hormone, *J. Exp. Zool.* 232:465–473 (1984).

H. R. Wilson et al., Abdominal Fat Pad Reduction in Broilers with Thyroactive Iodinated Casein, *Poultry Sci.* 62:811–818 (1983).

D. F. Wise et al., Growth Performance and Carcass Merit of Lambs Treated with Growth Hormone Releasing Factor (GRF) or Somatotropin (ST), *J. Anim. Sci.* 66(Suppl.1):275 (1988) (Abstract).

ENDOCRINE MANIPULATION TO IMPROVE BODY COMPOSITION OF POULTRY

BACKGROUND OF THE INVENTION

This invention relates to a method for improving the carcass quality of poultry. An aspect of this invention relates to a manipulation of the hormone system of the poultry. Still another aspect of this invention relates to means and methods for altering blood levels of hormones in the bodies of poultry, which means and methods can be employed on a commercial scale.

DESCRIPTION OF THE PRIOR ART

A predominant cost in intensive production of poultry is the feed energy required for metabolism and growth. The metabolizable energy derived from feedstuffs is partitioned into energy for maintenance (i.e., thermoregulation and nutrient utilization) and the energy assimilated into animal product (meat or eggs). Advances in genetics, nutrition and management have provided producers with rapidly growing poultry produced for meat (broiler chickens, turkeys, and the like) that efficiently convert feed energy and nutrients into animal product. Unfortunately, excessive fat deposition is an undesirable consequence of the accelerated growth of poultry and high nutrient density of poultry rations. As the poultry reach market age, fat deposition—rather than protein accretion—becomes the principal component of weight gain. For example in broiler chickens, body fat represents from 7 to 20% of live market weight, with abdominal fat making up about 4% of total body weight. Since accumulation of excessive body fat is considered an economic loss to both the producer and consumer of poultry meat, recent research efforts have attempted to solve the problem of excessive fat deposition in the chicken's body. The inter-dependence of nutritional and genetic factors that determine accumulation of body fat precludes a uniform strategy for nutritional restriction of fat deposition. Furthermore, genetic selection against body fat would probably reduce live market weight as well as carcass quality.

Metabolically-active agents, such as hormones, appear to have the greatest potential for manipulating fat deposition and/or muscle development in animals raised for meat (see Kiernan et al., U.S. Pat. No. 4,407,819 issued Oct. 4, 1983). For example, injection of finishing pigs with purified porcine growth hormone (pGH) was found to increase growth rate by 10-14%, improve feed conversion by 7-19%, reduce carcass fat content by 18-25% and increase muscle mass by 24-36% (T. D. Etherton et al., *J. Anim. Sci.* 64: 433-443, 1987). Similarly, daily administration of natural or recombinant-derived bovine GH (bGH) to dairy cows can increase milk yield by 23 to 41% (D. E. Bauman et al., *J. Dairy Sci.* 68: 1352-1362, 1985).

In contrast, however, these discoveries are not easily applied to poultry. Daily injection of broiler chickens with natural or recombinant-derived chicken GH (cGH) does not stimulate growth; in fact, cGH treatment usually results in increased accumulation of body fat (F. C. Leung et al., *Endocrinology* 118: 1961-1965, 1985; S. S. Liou et al., *Poultry Sci.* 64(Suppl. 1): 136, 1985; W. H. Burke et al., *Endocrinology*, 1987). Apparently, endocrine regulation of growth and metabolism in domestic fowl is distinctly different from that described for food mammals since exogenous cGH treatment alone does not promote growth or improve productive efficiency. The following summary of the relevant poultry science literature provides some insight into the comlexity of the research findings in this field.

Earlier work suggested that a synthetic iodinated protein, possessing thyroxine ($T_4$) activity, could be used as a feed additive to increase egg production or growth rate of domestic fowl (H. W. K. Jennings, British Patent No. 601,469, published in May of 1948). Iodinated casein (i.e., protomone) with 1% $T_4$ activity was originally developed as a possible growth promoter for poultry and livestock. However, the incorporation of protomone into the feed of meat-type chickens depressed growth rate, reduced feed efficiency, lowered carcass quality, and increased mortality rate when fed throughout the growth cycle (H. R. Wilson et al., *Poultry Sci.* 62: 811-818, 1983).

Triiodothyronine ($T_3$) and $T_4$ can be directly incorporated into the feed of broiler chickens for the purpose of elevating serum or plasma levels of thyroid hormones (J. D. May, *Poultry Sci.* 59: 888-892, 1980; J. D. May, in *Aspects of Avian . . . Implications* (C. G. Scanes et al., eds.) Texas Tech Univ. Press 26: 185-189, 1982). This work has shown that treatment of normal broiler chickens with 0.25 to 1 parts per million (ppm) of dietary $T_3$ throughout the entire growth cycle reduced body weight gain and feed efficiency. In contrast, the same doses of dietary $T_4$ did not impair growth performance. The depressed growth rate and reduced feed efficiency of normal (euthyroid) broiler chickens fed 1 ppm $T_3$ throughout the growth cycle has led to the notion that dietary $T_3$ is detrimental to the growth and productive efficiency of poultry.

Attempts at using administration of exogenous GH to stimulate the growth of normal chickens have generally been unsuccessful. Daily intravenous injection of thyrotropin-releasing hormone (TRH) (1 or 10 $\mu$g/kg of body weight/day) or GH-releasing factor (GRF, 10 $\mu$g/kg of body weight/day) alone or in combination for 21 days failed to stimulate growth rate or improve feed efficiency of broiler chickens despite elevated plasma GH levels (F. C. Buonomo and C. A. Baile, *Dom. Anim. Endocrinol.* 4: 269-276, 1986). Most of the evidence for supporting the idea that exogenous GH is capable of promoting growth of broiler chickens is derived from studies on growth-compromised Leghorn (egg-type) chickens. In these studies, dwarf strains or hypophysectomized (i.e., pituitary gland surgically removed) Leghorns were given replacement doses of $T_3$, $T_4$ or GH (usually mammalian GH) alone or GH in combination with either $T_3$ or $T_4$ to determine the importance of these hormones in the normal growth process. The sex-linked dwarf Leghorn chicken has elevated plasma levels of both GH and $T_4$, whereas $T_3$ concentrations are greatly reduced. The depressed growth rate of dwarf strains of Leghorn chickens was restored to normal by supplementing their diets with either $T_3$ or $T_4$, or by the combination of $T_4$ with a daily injection of mammalian GH (J. A. Marsh et al., *Proc. Soc. Exp. Biol. Med.* 177: 82-91, 1984; and J. A. Marsh et al., *Proc. Soc. Exp. Biol. Med.* 175: 351-360, 1984). The importance of $T_3$ to the normal growth process was further demonstrated by the ability of exogenous $T_3$, rather than GH therapy, to correct the growth deficit of hypophysectomized Leghorn chickens (C. G. Scanes et al., *Growth* 50: 12-31, 1986). Although several studies have revealed distinct interactions between GH and the thyroid hormones in regulation of growth in chickens, this area clearly needs further research to develop a truely practical program of hormone manipulation which is useful on a commercial scale for normal, meat-type poultry.

Any hormonal treatment that restricts fat deposition while increasing carcass protein content could theoretically have a major impact on the cost and quality of poultry meat, and the formulation of poultry rations, but because poultry (particularly broiler chickens) are produced on such an enormous commercial scale, the treatment must satisfy a variety of practical criteria.

DEFINITIONS

Throughout this application, the following terms are used with the meanings indicated below.

"Finishing phase" or "finishing phase of the growth cycle" means the time period in the production of poultry after the major portion of the rapid growth of the avian species (e.g. broiler chickens and turkeys) has been completed. With modern broiler chicken production techniques, chickens grow to a high percentage of their live market weight in the first three to four weeks of life. Six or seven weeks of age is usually considered a market age for broiler chickens. Thus, the "finishing phase" for broiler chickens typically begins at about 3, 4 or (rarely) 5 weeks of age and lasts until slaughter, or at least until market age. In some embodiments of this invention, it may be desirable to permit the poultry to clear their bodies of any treatment for up to a week or so prior to slaughter. Thus, the "finishing phase" for broiler chickens can last as little as two weeks or as long as about five weeks, but in any case the rapid growth phase has been substantially completed before the "finishing phase" is underway. For turkeys, the growth cycle lasts longer (e.g. 15 to 25 weeks), hence the "finishing phase" begins after 6 weeks of age and may last longer than four or five weeks.

"Metabolically-active thyroid hormone" refers to the natural or synthetic iodinated D- or L- or DL-thyronine compounds or iodinated phenoxyphenol-substituted aliphatic carboxylic acids having more than 15%, preferably more than 50%, of the receptor binding capability of $T_3$ (3,3',5-triiodo-L-thyronine, alternatively O-[4-hydroxy-3-iodophenyl]-3,5-diiodo-L-tyrosine) and preferably at least 30% of the in vivo activity of $T_3$. "Receptor binding" is defined herein in accordance with M. B. Bolger et al., *J. Biol. Chem.* 255: 10271–10278 (1980). Preferred metabolically-active thyroid hormones are compounds of the formula I:

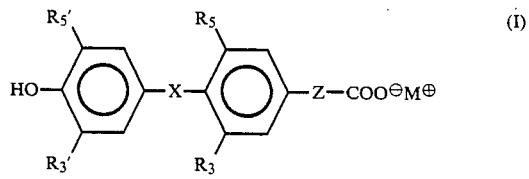

where Z is $C_1$-$C_4$ alkylene or amino-substituted $C_2$-$C_4$ alkylene;

$M^+$ is a physiologically acceptable cation such as $H^+$;

$R_3$ and $R_5$ are hydrogen or iodine, at least one of them being iodine;

$R_3'$ and $R_5'$ are hydrogen or iodine or —A—COO—$M^+$, where A is $C_2$-$C_4$ alkylene and $M^+$ is a physiologically acceptable cation; and X is a bridging radical such as —$CH_2$—, —S— or —O— (preferably —O—); provided, that if $R_3'$, $R_5'$, $R_3$ and $R_5$ are all iodine (I), then Z—COO$^-$ is a residue of the anion of acetic or propionic acid. The most active compounds of formula I are $T_3$ itself, "Triac" (Z=$CH_2$, M=H, $R_3$, $R_5$ and $R_3'$=I, $R_5'$=H) and "Tetrac" (similar to "Triac", except that $R_5'$=I). When Z is amino-substituted, the radical —Z—COO$^-$ can be the residue of D- or L- or DL-alanine.

BRIEF DESCRIPTION OF THE INVENTION

This invention is concerned with a novel, practical hormonal treatment for poultry grown for meat production, particularly broiler chickens, that dramatically reduces carcass fat and increases carcass protein content. The treatment comprises adding an effective amount, e.g. 0.01–5 parts per million, preferably 0.1 to 1 ppm of metabolically-active thyroid hormone, preferably triiodothyronine ($T_3$, 3,3',5-triiodo-L-thyronine or O-[4-hydroxy-3-iodophenyl]-3,5-diiodo-L-tyrosine), to feed of broiler chickens during the finishing phase (usually 3 to 6 weeks-of-age-). The consumption of feed containing 1 ppm $T_3$ provides broiler chickens with a 2- to 3-fold elevation of plasma $T_3$ levels when compared to controls. The efficacy of this invention is enhanced when, in addition to providing poultry with dietary $T_3$ during the finishing phase, GH (somatotropin) or glucagon levels in the bloodstream are also increased, also during the finishing phase and preferably by 2- to 10-fold. In one embodiment of this invention, poultry are provided with dietary $T_3$ during the finishing phase and circulating levels of glucagon relative to insuline are increased (i.e., the insulin-to-glucagon molar ratio is decreased). The timing of applying the dietary $T_3$ treatment alone or dietary $T_3$ in combination with other metabolically-active hormones (e.g. cGH or glucagon) to broiler chickens is of very great significance and should begin at the conclusion of the rapid growth phase (i.e., the start of the finishing phase) and should continue for a period of two to five weeks (i.e., until time of slaughter). There appears to be a greater advantage of applying the combination of dietary $T_3$ and cGH treatment. This treatment combination exerts a synergistic action, as indicated by more than 50% reduction on body fat content compared to only 17–25% reduction of body fat with dietary $T_3$ alone, and compared to essentially no fat reduction with cGH treatment alone. This novel manipulation of the bird's endocrine system has the advantage of dramatically reducing accumulation of excess body afat and increasing body protein content without impairing growth rate or feed efficiency.

This invention is not bound by any theory. Available data suggest that any hormone manipulation within the scope of this invention can have an impact upon the insulin-to-glucagon molar ratio of the avian pancreatic hormonal system (the I/G molar ratio). It is presently theorized that a decrease in the I/G molar ratio of poultry during the finishing phase mobilizes body fat stores, and, if sufficient metabolically-active thyroid hormone is present, body fat content is reduced.

DETAILED DESCRIPTION OF THE INVENTION

The above mentioned metabolically-active hormones are naturally synthesized within the body of domestic fowl and are known to be important regulators of various metabolic activities (i.e., energy, carbohydrate, lipid and protein metabolism) that conribute to normal growth and development. Within the scope of this invention, there are three major groups of metabolically-active hormones: (1) pituitary hormones [GH, prolactin and thyroid-stimulating hormone (TSH)] and their hypothalamic releasing factors [GH-releasing factor (GRF), GH-release inhibiting factor or somatostatin (SRIF), and thyrotropin-releasing hormone (TRH)], (2) the thyroid hormones ($T_3$ and $T_4$), and (3) the pancreatic hormones (insulin, glucagon and somatostatin). The natural metabolically-active hormones, synthetic analogues and their pharmacologically-acceptable salts are to be considered within the scope of this invention. Amino acid components or residues and carbohydrate components of synthetic metabolically-active substances are generally provided in the most active isomeric forms (e.g. L-amino acids, D-carbohydrates, etc.), except that racemates (DL-compounds), diastereomers, etc. can be used when at least 25% of the normal physiological activity is still obtained. Analogs of $T_3$ containing a D-amino acid residue can be active, apparently because of the importance of the location of other substituents on the molecules. This invention is concerned with means of enhancing circulating blood levels of certain metabolically-active hormones such as the thyroid hormones (particulary $T_3$), pituitary growth hormone and/or the pancreatic hormones.

The secretion of trophic hormones from the pituitary gland is regulated by releasing or inhibiting factors secreted by the hypothalamus. Within the scope of this invention, the releasing factors that regulate secretion of TSH and pituitary GH (somatotropin) are of particular interest. Thyrotropin-releasing hormone (TRH) stimulates the release of both TSH and GH from the avian pituitary gland into the bloodstream. Under the stimulating effect of TSH, the thyroid gland predominately synthesizes and secretes $T_4$ (3,5,3',5'-tetra-iodo-thyronine) into blood. The enzymatic activity of thyroxine-5'-monodeiodinase in peripheral tissue (particularly the liver and kidney) is responsible for converting $T_4$ into metabolically-active $T_3$. The positive or stimulative pathway is represented by: TRH→pituitary →TSH→thyroid→$T_4$→5'-monodeiodinase activity→$T_3$. It is generally accepted that $T_4$ is a prohormone without significant metabolic activity and that any benefit derived from treatment of animals with exogenous $T_4$ is derived from its conversion, via 5'-monodeiodinase activity, into metabolically-active $T_3$. Thus, the attempts at stimulating the growth or productive efficiency of domestic animals (poultry and livestock) with iodinated protein (i.e., protomone) that is based on thyroxine activity [see Jennings, British patent 601,469 dated May 6, 1948] are of questionable efficacy sjnce thyroxine ($T_4$) is essentially inactive in provoking metabolic and hormonal responses. In birds, circulating $T_3$ levels play an important role in regulating metabolic heat production and secretion of ituitary and pancreatic hormones. It is apparent from the working Examples which follow that $T_3$ also regulates the secretion of insulin and glucagon from the avian pancreas. All embodiments of this invention have in common the oral (preferably dietary) administration of metabolically-active thyroid hormone (preferably $T_3$ or a compound of Formula I, above, which has biological activity comparable to $T_3$) to poultry during the finishing phase, but not significantly prior to the finishing phase. During the finishing phase, the GH (somatotropin) naturally secreted by the poultry has already done much of its work, and there is no significant losses in body weight or protein content during this phase. There is, on the other hand, a more rapid utlization of body fat as a result of the orally-administered Formula I compound.

The other embodiments of this invention enhance or even synergize effectiveness of the metabolically-active thyroid hormone treatment by increasing blood levels of GH or by decreasing the insulin/glucagon (I/G) molar ratio. The timing of this enhancement effect need not be exactly coextensive with the metabolically-active thyroid hormone treatment, but it is believed to be useful to decrease the I/G molar ratio during the finishing phase, and insofar as GH also may depress the I/G molar ratio, GH treatment is also most useful during the finishing phase. In administring GH, it is preferred to match as closely as possible the natural timing of the pituitary release of this hormone, which follows a pattern characterized by a series of prominent peaks spaced an hour or two apart from one another. As a result, the plasma level of GH is preferably increased by 2- to 10-fold for only 15 to 30% of each day. This invention contemplates a variety of methods for elevating circulating levels of GH or enhancing secretion of GH from the avian pituitary gland. Chicken GH (cGH) can be purified from the pituitary of slaughtered birds (S. Harvey and C. G. Scanes, J. Endocrinol. 73: 321–329, 1977) or produced on the commercial scale by recombinant-DNA techniques (L. M. Souza et al., *J. Exp. Zool.* 232: 465–473, 1984; and W. H. Burke et al., *Endocrinology* 120: 651–658, 1987). The recombinant-derived cGH differs froom the naturally-occurring cGH mainly in the substitution of methionine as the N-terminal amino acid. The amino acid sequence and composition of cGH indicate that cGH shares about 77% homology with bovine GH (L. M. Souza et al., *J. Exp. Zool.* 232: 465–473, 1984).

| Chicken Growth Hormone | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | | | | | | | | | 10 | | | | | | | | | | 20 | | | | | | | | | | 30 | |
| 1 | T | F | P | A | M | P | L | S | N | L | F | A | N | A | V | L | R | A | Q | H | L | H | L | L | A | A | E | T | Y | K |
| 31 | E | F | E | R | T | Y | I | P | E | D | Q | R | Y | T | N | K | N | S | Q | A | A | F | C | Y | S | E | T | I | P | A |
| 61 | P | T | G | . K | D | D | A | Q | Q | K | S | D | M | E | L | L | A | F | S | L | V | L | I | Q | S | W | L | T | P | V |
| 91 | Q | Y | L | S | K | V | F | T | N | N | L | V | F | G | T | S | D | R | V | F | E | K | L | K | D | L | E | E | G | I |
| 121 | Q | A | L | M | R | E | L | E | D | R | S | P | R | G | P | Q | L | L | R | P | T | Y | D | K | F | D | I | H | L | R |
| 151 | N | E | D | A | L | L | K | N | Y | G | L | L | S | C | F | K | K | D | L | H | K | V | E | T | Y | L | K | V | M | K |
| 181 | C | R | R | F | G | E | S | N | C | T | I | | | | | | | | | | | | | | | | | | | | |

| Composition | | | | | | | | | | | |
|---|---|---|---|---|---|---|---|---|---|---|---|
| 13 | ALA | A | 9 | GLN | Q | 26 | LEU | L | 11 | SER | S |
| 11 | ARG | R | 14 | GLU | E | 14 | LYS | K | 12 | THR | T |
| 9 | ASN | N | 6 | GLY | G | 4 | MET | M | 1 | TRP | W |
| 11 | ASP | D | 4 | HIS | H | 11 | PHE | F | 8 | TYR | Y |

| Chicken Growth Hormone | | | | | | | | | |
|---|---|---|---|---|---|---|---|---|---|
| | | 4 | CYS | C | 6 | ILE | I | 9 | PRO | P | 8 | VAL | V |

Mol. wt. = 22,225
Number of residues = 191
(L.M. Souza et al., J. Exp. Zool. 232:465–473, 1984; and W. H. Burke et al., Endocrinology 120:651–658, 1987)

Purified and recombinant-derived cGH represent exogenous (i.e., produced outside the body) forms of cGH which are subject to parenteral administration. These exogenous preparations can be given by injection or implants that provide prolonged release of cGH (see Kent et al., U.S. Pat. No. 4,675,189 issued Jun. 23, 1987) especially during the finishing phase of the growth cycle in poultry.

Another method of enhancing blood levels of GH is by administration of the hypothalamic releasing factors that provoke endogenous GH secretion from the pituitary gland. Human GRF is a 44 amino acid polypeptide hormone wth a molecular weight of 5040 (R. Guillemin et al., Science 218: 585–587, 1982) that stimulates endogenous GH secretion from the pituitary gland (see Chang et al. U.S. Pat. No. 4,562,175 issued Dec. 31, 1985). Subsequent to the isolation and characterization of human GRF, the amino sequence has been determined for rat (J. Spiess et al., Nature 303: 532–535, 1983), porcine (P. Bohlen et al., Biochem. Biophys. Res. Comm. 116: 726–734, 1983), bovine (F. Esch et al., Biochem. Biophys. Res. Comm. 117: 772–779, 1983), caprine, and ovine (P. Brazeau et al., Biochem. Biophys. Res. Comm. 125: 606–614, 1984) forms of GRF. Apparently only the first 29 amino acids (i.e., GRF 1–29) are required for GH-releasing activity; therefore, numerous synthetic analogues have been developed that range from GRF 1–29 to GRF 1–44. Although an avian GRF has not yet been isolated and characterized, a number of these analogues possess the ability to provoke endogenous GH secretion from the chicken's pituitary (C. G. Scanes et al., Life Sci. 34: 1127–1134, 1984; and C. G. Scanes et al., J. Endocrinol. 108: 413–416, 1986). Within the context of this invention are all the pharmaceutical acceptable salts of the natural, recombinant-derived and synthetic analogues of GRF which stimulate GH secretion from the avian pituitary gland. The route of administration of GH or GRF can be oral, parenteral or by prolonged-release implant. Instead of administering cGH, a 191 amino acid protein hormone, exogenous GRF (a polypeptide hormone ranging from 1–29 to 1–44 amino acids) can be used to increase endogenous cGH secretion.

Another method of enhancing endogenous GH secretion in domestic fowl is the use of TRH—a tripeptide releasing factor (pyro-L-Glu-L-His-L-Pro-NH$_2$) secreted by the hypothalamus that provokes the secretion of GH, TSH and prolactin from the avian pituitary. Dialy intravenous injection of 1 to 10 μg TRH/day from 4 to 6 or 8 weeks-of-age is capable of increasing the growth rate of broiler chickens (Leung et al., U.S. Pat. No. 4,493,828 issued Jan. 15, 1985). An obvious advantage of using TRH treatment as a means of enhancing GH secretion in broiler chickens is that this hypothalamic releasing factor is orally-active and can be incorporated into the feed or drinking water of poultry (Snarey et al., U.S. Pat. No. 4,562,197, issued Dec. 31, 1985). The disadvantage of this approach of stimulating GH secretion is that TRH is a non-selective releasing factor which provokes the release of at least three pituitary hormones (i.e., TSH, GH and prolactin). Within the scope of this invention is the use of orally-active TRH applied in either the feed or drinking water of poultry to increase GH secretion during the finishing phase of the growth cycle.

Still another method of enhancing circulating blood levels of GH is the introduction of a fusion gene into somatic tissue or the germ line of poultry which leads to expression of copious amounts of GH in circulation (i.e., production of "transgenic chickens"). The microinjection of fertilized mouse ova with a hybrid fusion gene carrying the metallothionein (MT) promoter region and the structural gene which codes for either rat or human GH (i.e., a MT-GH fusion gene) results in a dramatic increase in body growth due to hypersecretion of GH (R. D. Palmiter et al., Nature 300: 611–615, 1982;and R. D. Palmiter et al., Science 222: 809–814, 1983). These transgenic mice typically show increases of 100- to 800-fold in serum GH levels and grow to twice the normal body size. Thus, gene insertion technology has tremendous potential for selective growth stimulation and/or improvements in productive efficiency of domestic animals. In fact, transgenic rabbits, pigs and sheep have been produced by microinjection of the MT-GH fusion gene (R. E. Hammer et al., Nature 315: 680–683, 1985). Furthermore, the introduction of a MT-GRF fusion gene into mice also results in increased body growth in the MT-GRF transgenic mice due to hypersecretion of GRF and, consequently, increased secretion of pituitary GH (R. E. Hammer et al., Nature 315: 413–416, 1985). However, the nature of ovulation and fertilization of the ovum in birds does not allow microinjection of hybrid fusion genes into the fertilized

| Human Growth Hormone-Releasing Factor | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| | | | | | | | | | 10 | | | | | | | | | | 20 | | | | | | | | | | 30 |
| 1 | Y | A | D | A | I | F | T | N | S | Y | R | K | V | L | G | Q | L | S | A | R | K | L | L | Q | D | I | M | S | R | Q |
| 31 | Q | G | E | S | N | Q | E | R | G | A | R | A | R | L—NH$_2$ | | | | | | | | | | | | | | | |

| Composition | | | | | | | | | | | |
|---|---|---|---|---|---|---|---|---|---|---|---|
| 5 | ALA | A | 5 | GLN | Q | 5 | LEU | L | 4 | SER | S |
| 6 | ARG | R | 2 | GLU | E | 2 | LYS | K | 1 | THR | T |
| 2 | ASN | N | 3 | GLY | G | 1 | MET | M | 2 | TYR | Y |
| 2 | ASP | D | 2 | ILE | I | 1 | PHE | F | 1 | VAL | V |

Mol. wt. = 5040
Number of residues = 44
R. Guillemin et al., Science 218:585–587, 1982 ovum. Souza et al. (*J. Exp. Zool.* 232: 465–473, 1984) have developed a recombinant retrovirus (i.e., a Rous sarcoma virus) vector that contains the entire coding region for cGH (designated SRA-cGH9). Infection of 9-day-old chicken embryos with the SRA-cGH9 retrovirus vector resulted in 3- to 10-fold increases in serum GH levels in the hatched chickens. Also within the scope of this invention is the development of transgenic chickens that carry a hybrid fusion gene for enhancing blood levels of metabolically-active hormones to be used in conjunction with dietary $T_3$ during the finishing phase.

Yet another method of increasing plasma GH levels is the use of neutralizing antibodies against somatostatin (SRIF) (see Maccecchini, U.S. Pat. No. 4,599,229, issued July 8, 1986). In normal pituitary function, SRIF inhibits secretion of GH and TSH from the pituitary gland; therefore, removal of the inhibitory effects of SRIF with neutralizing antibodies results in increased secretion of endogenous GH and, perhaps, TSH. Passive immunoneutralization of SRIF, achieved by injection of chickens with anti-SRIF antibodies raised in goats, sheep or rabbits, is capable of increasing plasma GH levels although body growth is not affected (G. S. G. Spencer et al., *Comp. Biochem. Physiol.* 85A: 553–556, 1986; and F. C. Buonomo et al., *Dom. Anim. Endocrinol.* 4: 191–200, 1987). In contrast, active immunoneutralization achieved by repeated injection (usually 3 injections made 2 to 3 weeks apart) of chickens with SRIF conjugated to a large immunogenic carrier protein (e.g., bovine serum albumin or human alpha-globulin), with the coupling agent glutaraldehyde, results in increased growth rate. With hybridoma technology, it is now feasible to produce sufficient quantities of mouse monoclonal antibody against SRIF for commercial use. Passive immunoneutralization of SRIF in chickens could be achieved indirectly by injecting the anti-SRIF monoclonal antibody into the broiler-breeder hens which would then deposit the monoclonal antibody into the fertilized egg before oviposition occurs, or directly by injecting the monoclonal anti-SRIF antibody either into the fertilized egg before (or during) incubation or into the bird after hatching. Within the definition of the present invention is the use of active or passive immunoneutralization of SRIF to enhance endogenous GH secretion during the finishing phase of the growth cycle of poultry in combination with providing dietary $T_3$.

SOMATOSTATIN-14

ALA-GLY-CYS-LYS-ASN-PHE-PHE-TRP-LYS-THR-PHE-THR-SER-CYS (Mol. wt.=1638)

The final embodiment of this invention is the manipulation of the molar ratio of insulin-to-glucagon (I/G) secreted into blood by the endocrine pancreas. Endocrine regulation of metabolism in birds is distinctly different from that of mammals because glucagon is the pancreatic hormone that regulates blood glucose levels in birds, and because fat synthesis (i.e., lipogenesis) takes place in the liver of birds (R. L. Hazelwood, in *Avian Physiology*, P. D. Sturkie, ed., Springer-Verlag, pp. 303–325, 1986). In birds, glucagon exerts a strong catabolic action by mobilizing free fatty acids from adipose tissue (i.e., a lipolytic action) whereas insulin promotes anabolic activities (i.e., glucose uptake, the formation and storage of glycogen, etc.). Thus, the I/G molar ratio serves as the prime determinant of metabolic homeostasis in birds (R. L. Hazelwood, *J. Exp. Zool.* 232: 647–652, 1984). A high I/G molar ratio indicates that the bird is in an anabolic mode (i.e., nutrient storage) while a low I/G molar ratio reflects the catabolic state (i.e., nutrient utilization). The avian pancreas also produces an exceptionally large quantity of SRIF which is thought to be an important regulator of the I/G molar ratio. Of particular interest is the fact that pancreatic SRIF is a potent inhibitor of glucagon secretion in chickens; therefore, it appears that immunoneutralization of SRIF, designed to promote pituitary GH secretion, can also enhance glucagon secretion from the pancreas.

Experimentation carried out in support of this invention indicates that administration of exogenous ncGH by injection and $T_3$ by dietary treatment during the finishing phase of the chicken's growth cycle ultimately alters the I/G molar ratio. The metabolic events that lead to the dramatic depletion of body fat content are brought about by a reduction in the I/G molar ratio (i.e., reduced insulin and elevated glucagon levels in blood) and an increase in circulating $T_3$ levels. This concept is supported by the observation that dietary $T_3$ treatment alone depresses insulin secretion while glucagon secretion is increased (i.e., a reduced I/G molar ratio) and consequently decreases fat deposition in chickens. Treatment of chickens with propylthiouracil, a goitrogen that inhibits 5'-monodeiodinase activity and therefore the conversion of $T_4$ into $T_3$, induces a hypothyroid state that results in elevated plasma insulin levels and increased accumulation of body fat (K. L. Raheja et al., *Horm. Metab. Res.* 12: 51–55, 1980; and Example 1 below). Furthermore, there is sufficient experimental evidence to support the idea that providing poultry with dietary $T_3$ and exogenous glucagon (by injection, implant or orally-active analogues of glucagon) would achieve the same benefits and improvements in body composition as the combination of dietary $T_3$ with any other treatment that simultaneously enhances circulating GH concentrations. This invention contemplates the use of exogenous glucagon treatment in combination with dietary $T_3$ as the most simple version of an endocrine manipulation designed to reduce body fat content of poultry.

Glucagon is a highly conserved polypeptide hormone which has an identical amino acid sequence among mammals. Chicken and turkey glucagon differ from mammalian glucagon by the single substitution of serine (SER) for asparagine (ASN) at position 28 (R. L. Hazelwood, *J. Exp. Zool.* 232: 647–652, 1986). The amino acid sequence of duck glucagon differs from other birds (chicken and turkey) due to the single substitution of threonine (THR) for serine (SER) at position 16. Because of these structural similarities, the commercial preparations of glucagon from the pancreases of slaughtered cattle and swine have the same biological and metabolic activity as endogenous glucagon when injected into chickens (see Example 3 below).

| Chicken Glucagon | | |
|---|---|---|
| 10 | 20 | 30' |

-continued

| Chicken Glucagon | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| 1 | H | S | Q | G | T | F | T | S | D | Y | S | K | Y | L | D | S | R | R | A | Q | D | F | V | Q | W | L | M | S | T |

| Composition | | | | | | | | | | | | | | |
|---|---|---|---|---|---|---|---|---|---|---|---|---|---|---|
| 1 | ALA | A | 3 | GLN | Q | 2 | LEU | L | 2 | PHE | F | 1 | TRP | W |
| 2 | ARG | R | 1 | GLY | G | 1 | LYS | K | 5 | SER | S | 2 | TYR | Y |
| 3 | ASP | D | 1 | HIS | H | 1 | MET | M | 3 | THR | T | 1 | VAL | V |

Mol. wt. = 3,485
Number of residues = 29
R. L. Hazelwood, "Carbohydrate Metabolism", in Avian Physiology, P. D. Sturkie ed., Academic Press. pp. 303–325, 1986.

Orally-active drugs have been developed for increasing the I/G molar ratio in mammals, e.g. to combat certain mild forms of diabetes. Some of these drugs have the opposite effect in avian species; that is, they decrease the I/G molar ratio. Any agent which decreases the I/G molar ratio in birds can be substituted for exogenous glucagon treatment in this invention.

Because of the ease and convenience of administration of orally-active hormones or hormone stimulants or suppressants through poultry feed, one of the embodiments of this invention involves a finishing feed which contains physiologically effective amounts of metabolically-active thyroid hormone (preferably $T_3$), alone or in combination with other orally-active compounds which stimulate or suppress hormone secretion. Finishing feeds typically contain a major amount (e.g. 60–90% by weight) of ground-up grain (corn, soybeans, etc.), a modest amount of fat (e.g. <10%), salts, vitamin and mineral premixes, amino acids, etc. The protein content is typically above 15% (e.g. 17–25% by weight), and some fiber content should be present.

Regardless of which embodiment of this invention is used, no radical changes in feed compositions or daily ration weights are necessary; indeed, conventional finishing feed formulas and amounts (except for the addition of dietary thyroid hormone and, if desired, orally active GH- or glucagon-increasing agents) are fully operative in this invention. The health of the birds does not appear to be adversely affected, and essential body functions (e.g. thermoregulation) do not appear to be adversely affected. However, economically advantageous changes in energy and/or protein content of finishing feeds are made possible by this invention.

Referring now to broiler chickens as a benchmark for the beneficial effects of this invention, it must be noted that these chickens grow from a weight of 30 to 50 grams at hatching to about 1.5–3 or even as much as 5 kilograms of body weight at market age. Of this market weight, 15–20 wt.-% is protein, 2–3 wt.-% is inorganic (showing up as ash in proximate analysis of body composition), and more than 10 wt.-% (e.g. 10–20 wt.-%) is fat, which means that the protein:fat ratio (by weight) is likely to be at or below 1.5:1 and certainly well below 2:1. In broiler chickens treated according to this invention, however, protein:fat ratios above 1.6:1 and even above 2:1 have been obtained, due to decreases in carcass at content exceeding 15 wt.-%. A comparable increase in the protein:fat ratio was not obtained with $T_4$+GH treatment (although some improvement was found); $T_4$ treatment alone had almost no effect upon this ratio; and various other treatments actually seemed to decrease the protein:fat ratio at the doses tested (e.g. GH alone, TRH alone, TRH+GH, and propylthiouracil alone). In the Examples which follow, the principle and practice of this invention are illustrated. To provide maximum scientific control over the results, cGH and glucagon were administered by daily intramuscular injection even though this technique of administration would not normally be used in commercial practice. The following abbreviations are used in these Examples:

CF = control feed
$T_3$ = 3,3',5-triiodo-L-thyronine
$T_4$ = thyroxine
PTU = propylthiouracil
TRH = thyrotropin-releasing hormone
GH = growth hormone (e.g. ncGH, natural chicken GH)
BW = body weight
ADG = average daily weight gain
ADFC = average daily feed consumption
BI = bicarbonate buffer injection
N = number of test chickens
SEM = standard error of the mean
NIC = non-injected control
BC = sodium acetate buffer-injected control
BSA = bovine serum albumin
IgG = chicken immunoglobulin G
SRIF = somatostatin or somatotropin-release inhibiting factor

EXAMPLE 1

THE EFFECT OF THYROID MANIPULATION AND CHICKEN GROWTH HORMONE INJECTIONS ON GROWTH, FEED EFFICIENCY AND BODY COMPOSITION OF BROILER COCKERELS

MATERIALS AND METHODS

The purpose of this study was to determine the effect manipulating blood levels of thyroid hormones and/or growth hormone on growth performance and body composition of broiler chickens. The following thyroid-active substances were purchased from Sigma Chemical Company (St. Louis, Mo.): Product T 2877 (3,3',5-triiodo-L-thyronine or $T_3$), Product T 2376 (3-[4-(4-hydroxy-3,5-diiodophenoxy)-3,5-diiodophenyl]-L-alanine or $T_4$), Product P 9012 (L-pyroglutamyl-L-histidyl-L-prolinamide or TRH), and Product P 3755 (6-N-propyl-2-thiouracil or PTU). Purified natural chicken growth hormone (ncGH) was obtained from the Research and Education Center, Harbor-UCLA Medical Center, Torrance, Calif. A premix was prepared by thoroughly mixing the required quantity of thyroid-active substance (50 mg of $T_3$, 50 mg of $T_4$, 250 mg TRH) into 200 g of dextrose. The premix (200 g) was then used to prepare 50 kg batches of each experimental diet according to the formula for broiler-finisher ration described in Table 1. The diet containing 0.5% PTU was prepared by mixing 250 g of PTU into 49.75 kg of the basal ration (Table 1). The following dietary levels were thus achieved: 1 ppm $T_3$, 1 ppm $T_4$, 5 ppm TRH, 0.5% PTU, or control feed (CF).

Broiler cockerels (Ross X Arbor Acre strain) were raised to 3 weeks-of-age in a battery-brooder and then transferred to wire grow-out cages (4 birds/pen) held in two controlled-environment rooms (10 pens/room). Beginning at 3 weeks of age, eight birds (2 pens of 4 birds) were randomly assigned to each of 10 treatments. The chickens were provided the experimental diets and water ad libitum. The five dietary treatments (CF, $T_3$, $T_4$, TRH and PTU) were designated for convenience in presentation of data as Group 1. The remaining five treatments (Group 2) consisted of a dietary treatment (with the exception of PTU) plus a single daily intramuscular injection of 100 ug ncGH/kg body weight [i.e., CF+buffer injection (CF+BI), CF+GH, $T_3$+GH, $T_{4+GH}$, and $TRH+GH$]. For injection, the ncGH was reconstituted in sterile 0.025M sodium bicarbonate buffer (pH 9.8). The 10 treatments were administered for 21 days (i.e., from 3 to 6 weeks of age).

Measurement of body weight and feed consumption at weekly intervals allowed calculation of the average daily gain (ADG, g/bird/day), average daily feed consumption (ADFC, g/bird/day) and the feed-to-gain ratio (FTG, kg feed/kg gain) over the 21 day experimental period. Blood samples were taken each week (4, 5, and 6 weeks) just before (pre-injection) and 4 hours post-injection of ncGH. Specific radioimmunoassays were used to measure plasma levels of cGH (J. A. Proudman, *Proc. Soc. Exp. Biol. Med.* 175: 417–419, 1984), $T_3$ and $T_4$ (L. A. Cogburn and R. M. Freeman, *Gen. Comp. Endocrinol.* 68: 113–123, 1987), insulin and glucagon (P. C. Allen and J. P. McMurtry, *Poultry Sci.* 63: 1129–1135, 1984). At the conclusion of the study, birds were killed and the carcasses frozen for proximate analysis. The frozen carcasses were ground in a meat grinder and aliquots of each ground carcass taken for determination of moisture, protein, fat and ash by established analytical procedures (*Official Method of Analysis*, Edition 13, W. Horwitz ed., Association of Official Analytical Chemist, Washington, D.C., 1980). Body composition data are presented as a percent of live weight at 6 weeks-of-age. Least squares regression analysis was used to test for significant differences (P<0.05) due treatment.

TABLE 1

Composition of Broiler-Finisher Ration

| Ingredients | % |
|---|---|
| Corn, yellow, ground | 64.88 |
| Soybean meal, 48% | 21.23 |
| Poultry by-product meal | 3.50 |
| Corn gluten meal, 60% | 4.00 |
| Blended fat | 3.31 |
| Defluoridated phosphate | 1.71 |
| Limestone | 0.47 |
| Livestock salt (NaCl) | 0.170 |
| L-lysine | 0.170 |
| D,L-methionine | 0.060 |
| Trace mineral premix | 0.050 |
| Vitamin premix | 0.050 |
| Hormone/dextrose premix | 0.400 |
| Grand total | 100% |
| Analysis | |
| Protein | 20.7% |
| Fat | 6.5% |
| Fiber | 2.4% |
| Metabolizable Energy | 3244 kcal/kg |

RESULTS

GROWTH PERFORMANCE

The final body weight of hypothyroid PTU-treated chickens was 18% lower (P<0.05) than that of birds fed CF or thyroid hormones (Table II). Although not significantly different, TRH-fed birds had a 6% higher body weight (BW), a 9% higher ADG and a 11% higher ADFC rate than the CF group. Dietary $T_3$ treatment did not affect growth rate or feed efficiency of broiler chickens. In contrast, hypothyroidism induced by dietary PTU depressed growth rate and reduced feed conversion. The combination of exogenous cGH treatment with dietary $T_3$ or $T_4$ reduced the final BW, ADG and ADFC by 12 to 15% when compared to the CF+BI group (Table III). Compared to the FTG ratio of the CF+BI group, feed efficiency was improved (P<0.05) by 9% in the CF+GH group and by 5% in the TRH+GH treatment.

TABLE II

Growth and Feed Efficiency of Broiler Cockerels Fed Thyroid-active Substances (Group 1)

| Treatment | BW (kg) | ADG | ADFC | FTG |
|---|---|---|---|---|
| CF | 1.74 ± .01[a] | 52.0 ± 2.1[ab] | 112.9 ± 0.7[ab] | 2.18 ± .10[ab] |
| 1 ppm $T_3$ | 1.70 ± .09[a] | 48.8 ± 4.3[b] | 101.1 ± 5.2[b] | 2.08 ± .08[b] |
| 1 ppm $T_4$ | 1.76 ± .04[a] | 51.9 ± 3.3[ab] | 108.4 ± 3.6[b] | 2.09 ± .06[b] |
| 5 ppm TRH | 1.85 ± .08[a] | 56.5 ± 0.2[a] | 125.2 ± 5.5[a] | 2.21 ± .01[ab] |
| 0.5% PTU | 1.42 ± .05[b] | 39.2 ± 4.0[c] | 92.3 ± 7.9[c] | 2.36 ± .04[a] |

Means (± SEM) within a column possessing a different superscript are significantly (P < 0.05) different.

TABLE III

Growth and Feed Efficiency of Broiler Cockerels Fed Thyroid Active Substances and Injected Daily with ncGH (Group 2)

| Treatment | BW (kg) | ADG | ADFC | FTG |
|---|---|---|---|---|
| CF + BI | 1.77 ± .04[a] | 53.3 ± 1.3[a] | 118.4 ± 1.2[a] | 2.22 ± .08[a] |
| CF + GH | 1.83 ± .04[a] | 57.0 ± 0.4[a] | 115.8 ± 1.8[ab] | 2.03 ± .02[c] |
| $T_3$ + GH | 1.58 ± .06[b] | 46.2 ± 3.9[b] | 102.6 ± 6.7[bc] | 2.22 ± .04[a] |
| $T_4$ + GH | 1.54 ± .07[b] | 44.8 ± 0.6[b] | 97.7 ± 1.9[c] | 2.18 ± .01[ab] |
| TRH + GH | 1.75 ± .07[ab] | 53.5 ± 0.3[a] | 113.3 ± 1.2[ab] | 2.12 ± .01[b] |

Means (± SEM) within a column possessing a different superscript are significantly (P < 0.5) different.

BODY COMPOSITION

The PTU treatment increased (P<0.05) body fat content by 50% at the expense of body ash, protein and water when compared to the CF group (Table IV). In contrast, dietary $T_3$ alone reduced body fat content by 17% while body protein and water were slightly increased. Dietary TRH increased body fat content by 12% although not significantly different from the CF birds. Dietary $T_3$ plus exogenous cGH treatment reduced (P<0.05) body fat content by 51% while the ash, protein and water contents were increased by 6 to 9% above that of the CF+BI group (Table V). The combination of dietary $T_4$ and daily cGH injection improved body composition since body fat was reduced (P<0.05) by 26% when compared to the CF+BI group.

TABLE IV

Body Composition of Broiler Chickens Fed Thyroid-active Substances (Group 1)

| Treatment | N | % BW | | | |
|---|---|---|---|---|---|
| | | Water | Protein | Fat | Ash |
| CF  | 8 | 66.4 ± .54$^b$ | 17.8 ± .46$^a$ | 12.1 ± .67$^{bc}$ | 2.32 ± .02$^{ab}$ |
| $T_3$  | 8 | 68.6 ± 1.0$^a$ | 18.4 ± .22$^a$ | 10.1 ± 1.2$^c$ | 2.19 ± .05$^{bc}$ |
| $T_4$  | 8 | 65.8 ± .29$^b$ | 18.2 ± .31$^a$ | 12.9 ± .41$^{bc}$ | 2.35 ± .03$^a$ |
| TRH | 8 | 65.5 ± .73$^b$ | 18.1 ± .21$^a$ | 13.6 ± .88$^b$ | 2.34 ± .06$^{ab}$ |
| PTU | 8 | 61.9 ± .73$^c$ | 17.2 ± .20$^b$ | 18.2 ± .80$^a$ | 2.17 ± .06$^c$ |

Means (± SEM) within a column possessing a different superscript are significantly (P < 0.05) different.

TABLE V

Body Composition of Broiler Chickens Fed Thyroid-active Substances and Injected Daily with ncGH (Group 2)

| Treatment | N | % BW | | | |
|---|---|---|---|---|---|
| | | Water | Protein | Fat | Ash |
| CF + BI | 8 | 64.7 ± .32$^c$ | 18.3 ± .18$^b$ | 14.6 ± .47$^a$ | 2.34 ± .05$^{ab}$ |
| CF + GH | 8 | 64.7 ± .51$^c$ | 18.1 ± .15$^b$ | 14.5 ± .52$^a$ | 2.20 ± .04$^b$ |
| $T_3$ + GH | 8 | 70.4 ± .46$^a$ | 19.3 ± .12$^a$ | 7.1 ± .57$^c$ | 2.51 ± .04$^a$ |
| $T_4$ + GH | 8 | 67.3 ± .46$^b$ | 18.6 ± .19$^b$ | 10.8 ± .57$^b$ | 2.47 ± .07$^{ab}$ |
| TRH + GH | 8 | 65.9 ± .62$^{bc}$ | 18.4 ± .11$^b$ | 13.0 ± .66$^a$ | 2.22 ± .06$^b$ |

Means (± SEM) within a column possessing a different superscript are significantly (P < 0.05) different.

PLASMA HORMONE CONCENTRATIONS

The average plasma $T_3$ level of $T_3$-fed birds was 2.6-times higher (P<0.05) than that of birds in the CF, TRH or $T_4$ treatments (3 ng/ml) (Group 1). In contrast, the average $T_3$ level in the PUT-treated birds (1.5 ng/ml) was 53% lower (P<0.05) than the CF birds. Compared to the average of CF and TRH treatments, plasma $T_4$ levels were 9.6-times higher (P<0.05) in $T_4$-fed birds and reduced (P<0.05) by 58% in $T_3$-fed birds and by 76% in PTU-fed birds. Plasma GH levels were 1.9-times higher in PTU-fed birds and 32% lower in $T_3$-fed birds compared to the CF treatment. The plasma insulin/glucagon (I/G) molar ratio (i.e., increased glucagon and reduced insulin levels) of $T_3$-fed birds was 4.3-times lower (P<0.05) than that of CF birds (2.18) (Table VI). In contrast, the I/G molar ratio of PTU-treated birds was 2.9-times greater (P<0.05) than that of the CF group.

In Group 2, the average plasma GH concentration at 4 hours post-injection of 100 μg ncGH/kg BW (62 ng/ml) was 3-times higher (P<0.05) than the pre-injection GH concentration. The combination of daily cGH injection with dietary thyroid hormone reduced (P<0.05) the plasma I/G molar ratio by 6.8-fold in $T_3$-fed birds and by 2.2-fold in $T_4$-fed birds (Table VII). Clearly, these data indicate that elevated plasma $T_3$ levels inhibit insulin secretion whereas glucagon secretion is enhanced. The simultaneous elevation of cGH and $T_3$ levels in plasma potentiate this effect and lead to a dramatic reduction in deposition of body fat in broiler chickens.

TABLE VI

Plasma Concentration of Pancreatic Hormones in Broiler Chickens Fed Thyroid-active Substances (Group 1)

| Treatment | N | pg/ml | | I/G Molar Ratio |
|---|---|---|---|---|
| | | Insulin (I) | Glucagon (G) | |
| CF  | 24 | 1038$^b$ | 289$^{ab}$ | 2.18$^b$ |
| $T_3$  | 24 | 409$^c$ | 491$^a$ | 0.51$^c$ |
| $T_4$  | 24 | 776$^{bc}$ | 318$^{ab}$ | 1.49$^{bc}$ |
| TRH | 24 | 814$^{bc}$ | 295$^{ab}$ | 1.68$^{bc}$ |
| PTU | 24 | 2349$^a$ | 225$^b$ | 6.35$^a$ |

The I/G molar ratio was calculated from plasma insulin and glucagon levels in each plasma sample assuming molecular weights of 5734 for insulin and 3485 for glucagon.

Means (± SEM) within a column possessing a different superscript are significantly (P < 0.05) different.

TABLE VII

Plasma Concentration of Pancreatic Hormones in Broiler Chickens Fed Thyroid-active Substances and Injected Daily with ncGH (Group 2)

| Treatment | N | pg/ml | | I/G Molar Ratio |
|---|---|---|---|---|
| | | Insulin (I) | Glucagon (G) | |
| CF + BI | 24 | 1323$^a$ | 313$^b$ | 2.57$^a$ |
| CF + GH | 24 | 1107$^b$ | 298$^b$ | 2.28$^a$ |
| $T_3$ + GH | 24 | 249$^d$ | 410$^a$ | 0.38$^c$ |
| $T_4$ + GH | 24 | 598$^c$ | 314$^b$ | 1.19$^b$ |
| TRH + GH | 24 | 1047$^b$ | 338$^{ab}$ | 1.92$^a$ |

Means (± SEM) within a column possessing a different superscript are significantly (P < 0.05) different.

EXAMPLE 2

THE EFFECT OF DIETARY $T_3$ AND ncGH INJECTION ON GROWTH, FEED EFFICIENCY, AND BODY COMPOSITION OF BROILER COCKERELS

MATERIALS and METHODS

The purpose of this study was to confirm the original finding of a synergism between exogenous cGH and dietary $T_3$ in reducing deposition of body fat in broiler chickens (Example 1). Forty-eight 3-week-old broiler cockerels (Ross X Arbor Acre) were randomly divided into four treatment groups that contained three pens of four birds. The birds were housed in a controlled-environment room under a 20 hour light/4 hour dark cycle with feed and water provided ad libitum. The four treatment groups were: control feed (CF)+buffer injection (BI), 1 ppm dietary $T_3$+BI, CF+GH injection (100 μg/kg BW/day), and 1 ppm dietary $T_3$+GH injection (100 μg/kg BW/day. The basal feed ration was formulated according to the ingredient composition in Table I.

The birds were continuously provided with CF or feed containing 1 ppm $T_3$ from 3 to 6 weeks-of-age. Each bird in the CF+GH and $T_3$+GH treatment groups received a single intramuscular injection of 100 μg ncGH/kg BW each day for 21 days. The preparation of ncGH used in this study was from the same lot used in Example 1. Birds in the CF+BI and $T_3$+BI treatments received a single intramuscular injection of 0.5 ml 0.025M sodium bicarbonate buffer (pH 9.8) each day for 21 days.

Body weights and feed consumption was determined at weekly intervals although the ADG, ADFC and FTG ratio was determined over the 21 day period. Blood samples were taken each week (4, 5 and 6 weeks-of-age) just before (pre-injection) and four hours post-injection of ncGH. At the conclusion of the study (6 weeks-of-age), birds were killed and the abdominal fat removed and weighed. The liver and abdominal fat were returned to the carcass which was frozen for proximate analysis as described in Example 1.

RESULTS

The ADG, ADFC and FTG ratio was not affected by dietary $T_3$, daily ncGH injection or the combination of $T_3$+GH treatments (Table VIII). There was no significant effect of treatment on either the final (6 week) body weight or the relative liver weight (Table IX-A). However, dietary $T_3$ treatment alone reduced (P<0.05) the abdominal fat content by 28% whereas the combination of $T_3$+GH treatments was twice (P<0.05) as effective in reducing abdominal fat content (i.e., a 55% reduction). Daily injection of ncGH alone (CF+GH) did not affect growth performance, final body weight, relative liver weight or absominal fat content. Body fat content (%BW) was reduced by 16% in $T_3$-fed birds and by 30% in birds given the $T_3$+GH treatment combination (Table IX-B). The body water and ash contents were also increased in birds treated with $T_3$ alone or in combination with GH injection.

The average plasma GH concentration at 4 hours post-injection of 100 μg ncGH/kg BW at 4, 5 and 6 weeks-of-age was 4-times higher than the pre-injection plasma GH levels. The average plasma $T_3$ level in the $T_3$+BI and $T_3$+GH treatment groups was 2.3-times higher than that of birds given the CF+BI or CF+GH treatment.

TABLE VIII

Growth and Feed Efficiency of Broiler Chickens Fed Triiodothyronine ($T_3$) and Injected Daily with ncGH

| Treatment | N | ADG | ADFC | FTG |
|---|---|---|---|---|
| CF + BI | 3 | 53.5 ± 0.5 | 118.5 ± 1.8 | 2.21 ± .02 |
| $T_3$ + BI | 3 | 52.6 ± 1.0 | 117.9 ± 0.8 | 2.24 ± .03 |
| CF + GH | 3 | 53.0 ± 2.8 | 115.4 ± 3.5 | 2.18 ± .05 |
| $T_3$ + GH | 3 | 49.5 ± 4.1 | 111.2 ± 6.0 | 2.26 ± .07 |

Each value represents the mean (± SEM) of three pens (4 birds/pen) over the three week experimental period (e.g., N = 3).

TABLE IX-A

Final Body Weight and Relative Weight (% BW) of the Liver and Abdominal Fat of Broiler Cockerels Fed Triiodothyronine ($T_3$) and Injected Daily with ncGH

| Treatment | N | Body Weight (BW,kg) | Liver (% BW) | Abdominal Fat (% BW) |
|---|---|---|---|---|
| CF + BI | 12 | 1.86 ± .060 | 2.91 ± .239 | 2.57 ± .129$^a$ |
| $T_3$ + BI | 12 | 1.86 ± .048 | 2.54 ± .096 | 1.86 ± .396$^b$ |
| CF + GH | 12 | 1.88 ± .051 | 2.74 ± .102 | 2.56 ± .178$^a$ |
| $T_3$ + GH | 12 | 1.77 ± .071 | 2.80 ± .059 | 1.16 ± .143$^c$ |

Means (± SEM) within a column possessing a different superscript are significantly (P < 0.05) different.

TABLE IX-B

Body Composition of Broiler Cockerels Fed Triiodothyronine ($T_3$) and Injected Daily with ncGH

| Treatment | N | % BW Water | Protein | Fat | Ash |
|---|---|---|---|---|---|
| CF + BI | 12 | 63.5 ± .34$^c$ | 17.2 ± .29 | 15.7 ± .33$^a$ | 2.31 ± .073$^{ab}$ |
| $T_3$ + BI | 12 | 65.5 ± .60$^b$ | 17.3 ± .36 | 13.2 ± .62$^b$ | 2.40 ± .054$^a$ |
| CF + GH | 12 | 63.7 ± .33$^{bc}$ | 17.0 ± .17 | 15.9 ± .32$^a$ | 2.23 ± .058$^b$ |
| $T_3$ + GH | 12 | 67.7 ± .46$^a$ | 17.2 ± .16 | 11.0 ± .54$^c$ | 2.39 ± .028$^a$ |

Means (± SEM) within a column possessing a different superscript are significantly (P < 0.05) different.

EXAMPLE 3

EFFECT OF DAILY INJECTION OF GLUCAGON ON GROWTH, FEED EFFICIENCY AND BODY COMPOSITION OF BROILER COCKERELS

MATERIALS AND METHODS

The purpose of this experiment was to determine if treatment of broiler chickens with exogenous glucagon alone would affect the growth performance or body composition. Crystalline bovine/porcine glucagon was obtained from Sigma Chemical Co. (Product G 4250) and further purified by high-performance liquid chromatography (HPLC) for injection. The glucagon was dissolved in sterile 0.02M sodium acetate buffer (pH 5.5) containing 1.6% glycerin.

Thirty-two 4-week-old broiler cockerels (Ross X Arbor Acre) were randomly assigned to eight pens containing four birds each. The four treatments were:

non-injected control (NIC), sodium acetate buffer-injected control (BC), 125 μg/kg BW twice/day (or 250 μg/kg BW/day), and 250 ug/kg BW twice/day (or 500 μg/kg BW/day) for 14 days (i.e., 4 to 6 weeks-of-age). The first injection was given between 1000 to 1100 hour while the second injection of the day was given betwen 1400 to 1500 hour. Blood samples were taken just before the second daily injection (pre-injection) and 30 minutes post-injection at 5 and 6 weeks-of-age. The measurements of growth performance and body composition were the same as those in Example 1.

RESULTS

Two daily injections of glucagon did not affect the final (6 weeks) body weight, ADG or ADFC of broiler chickens (Table X). The highest dose of glucagon (500 μg/kg/day) reduced ($P<0.05$) feed efficiency as indicated by a 9% increase in the FTG ratio. The relative liver weight was increased by 30% in the 250 μg/kg BW/day group and by 53% in the 500 μg/kg BW/day group when compared to that of the BC group (2.49% BW). When compared to the BC group, the highest daily dose of glucagon (500 μg/kg) increased ($P<0.05$) the body fat content of broiler chickens by 12% (Table XI). Daily injections of glucagon increased plasma levels of free fatty acids (an index of lipolysis) by 4- to 6-fold at 30 minutes post-injection. However, the net effect of glucagon treatment was increased accumulation of body fat. There was no effect of glucagon treatment on plasma levels of GH, $T_3$ or $T_4$. Therefore, these data indicate that glucagon treatment per se can not be used to reduce body fat content of chickens although increased glucagon secretion is apparent in chickens fed $T_3$ alone or $T_3$ in combination with daily injection of ncGH (Example 1). However, the combination of dietary $T_3$ with exogenous glucagon can also reduce the body fat content of poultry.

TABLE X

Growth and Feed Efficiency of Broiler Cockerels Given Two Daily Injections of Glucagon[1]

| Treatment | BW (kg) | ADG | ADFC | FTG |
|---|---|---|---|---|
| NIC | 2.27 ± .07 | 75.3 ± 1.8 | 159.5 ± 0.9 | 2.12 ± .01[b] |
| BC | 2.18 ± .06 | 68.0 ± 3.8 | 147.3 ± 9.5 | 2.16 ± .02[b] |
| 250 μg/kg/day | 2.33 ± .06 | 76.6 ± 1.0 | 166.9 ± 1.4 | 2.18 ± .05[ab] |
| 500 μg/kg/day | 2.20 ± .05 | 69.2 ± 3.6 | 162.9 ± 5.3 | 2.36 ± .05[a] |

[1]The four treatment groups were non-injected controls (NIC), buffer-injected controls (BC), 125 μg/kg twice a day (250 μg/kg/day), and 250 μg/kg twice a day (500 μg/kg/day).
Means (± SEM) within a column possessing a different superscript are significantly ($P < 0.05$) different.

TABLE XI

Body Composition of Broiler Cockerels Given Two Daily Injections of Glucagon

| Treatment | N | % BW | | | |
|---|---|---|---|---|---|
| | | Water | Protein | Fat | Ash |
| NIC | 8 | 61.2 ± .59 | 17.2 ± .17 | 18.2 ± .68[ab] | 2.29 ± .08 |
| BC | 8 | 62.3 ± .76 | 17.4 ± .16 | 17.4 ± .76[b] | 2.30 ± .06 |
| 250 μg/day | 8 | 61.5 ± .30 | 17.1 ± .11 | 18.6 ± .30[ab] | 2.16 ± .07 |
| 500 μg/day | 8 | 60.6 ± .64 | 16.9 ± .22 | 19.4 ± .44[a] | 2.17 ± .03 |

Body composition is expressed as a percent of final body weight (% BW).
Means (± SEM) within a column possessing a different superscript are significantly ($P < 0.05$) different.

EXAMPLE 4

EFFECT OF ACTIVE SOMATOSTATIN IMMUNONEUTRALIZATION ON GROWTH RATE AND ABDOMINAL FAT OF BROILER COCKERELS

MATERIALS AND METHODS

The purpose of this experiment was to determine if active immunization of chickens against somatostatin (SRIF) conjugated to either bovine serum albumin (BSA) or chicken immunoglobulin G (IgG) would affect growth rate, abdominal fat content or plasma GH levels of broiler chickens. The coupling agent used to conjugate SRIF to either BSA or chicken IgG was 1-ethyl-3-(3-dimethylaminopropyl)-carbodiimide (ECDI) (Product E 7750, Sigma).

Two grams of BSA (Product A 7888, Sigma) were dissolved in 10 ml of 0.05M phosphate buffer pH 7.0 (200 mg/ml). Five milligrams (mg) of SRIF (Product S 9129, Sigma) were dissolved in 1 ml of the phosphate buffer (5 mg/ml). The ECDI was prepared by dissolving 2 g of ECDI in 5 ml of 0.05M phosphate buffer. The conjugation was achieved by first adding 4 mg of SRIF (0.8 ml) and 10 mg of BSA (0.05 ml) to a 10 ml polypropylene vial and then 10 mg of ECDI (0.025 ml) was added. The mixture was stirred at room temperature for 30 minutes and an additional 0.025 ml of ECDI was added. Following an additional 30 minutes, 2.1 ml of phosphate buffer was added to the reaction vial and the contents transferred to dialysis tubing with a molecular weight cut-off of 3500. The SRIF-BSA conjugate was dialyzed against 550 ml of 0.05M phosphate buffer at 4° C. for 48 hours. The optical density of the dialysate was measured at 280 nm to determine the concentration of unconjugated SRIF removed by dialysis. Approximately 1.9 mg of SRIF was conjugated to 10 mg of BSA.

Ten milligrams of chicken IgG (Cappel Product 6004-0080, Organon Teknika Corp., Malvern, Penn.) and 5 mg of SRIF (Sigma) were dissolved in 1.1 ml of 0.05M phosphate buffer in a 10 ml polypropylene vial. Then, 10 mg of ECDI (0.025 ml) were added and the solution was mixed at room temperature for 30 min; an additional 10 mg of ECDI was then added. Following the second 30 minute reaction time, 1.85 ml of phosphate buffer as added and the contents transfer to dialysis tubing (3500 molecular weight cut-off). The SRIF-IgG conjugate was dialyzed against 600 ml of 0.05M phosphate buffer for 48 hours at 4° C. Measurement of the optical density of the dialysate at 280 nm allowed calculation of unconjugated SRIF by the extinction coefficient method. Approximately 2.65 mg of SRIF was conjugated to 10 mg of chicken IgG.

The dosage of conjugate to be used for the immunization studies were based on 0.10 mg SRIF content in the conjugate. The immunogen was prepared by diluting 600 μg of each SRIF conjugate (SRIF-BSA or SRIF-IgG) to a final volume of 3 ml which was then emulsified with 3.0 ml of Freund's complete adjuvant. The control immunogen (BSA) was prepared by emulsifying 3.2 mg of BSA (3 ml) with 3 ml of Freund's complete adjuvant. Fifteen 4-week-old broiler cockerels were randomly divided into three groups or pens (BSA-Control, SRIF-BSA and SRIF-IgG treatments). Each bird was injected with 1 ml of the emulsion, containing 0.10 mg SRIF peptide in the conjugate for the SRIF-BSA and SRIF-IgG groups and 0.53 mg BSA for the BSA-Control group, given at two intramuscular sites and one subcutaneous site. At 6 weeks-of-age, each bird was given a 1 ml booster immunization containing 0.10 mg of SRIF (SRIF-BSA or SRIF-IgG) or 0.53 mg BSA (BSA-Control group) emulsified in Freund's incomplete adjuvant. Body weights and feed consumption per pen of five birds were determined at weekly intervals for four weeks (i.e., until 8 weeks-of-age). A 5 ml blood sample was obtained from each bird at 6, 7 and 8 weeks-of-age for measurement of plasma GH levels. At 8 weeks-of-age, the birds were killed and the abdominal fat removed and weighed.

RESULTS

TABLE XII

Final Body Weight and Relative Weight of Abdominal Fat in Broiler Chickens Actively Immunized Against Somatostatin

| Treatment | N | Final BW (kg) | Abdominal Fat (% BW) |
|---|---|---|---|
| BSA-Control | 5 | 3.19 | 2.44 |
| SRIF-BSA | 5 | 3.12 | 3.04 |
| SRIF-IgG | 5 | 3.34 | 2.81 |

Final body weight (BW) was determined at 8 weeks of age.

TABLE XIII

Plasma Growth Hormone Levels (ng/ml) in Broiler Chickens Actively Immunized Against Somatostatin

| Treatment | N | Age (wk) | | |
|---|---|---|---|---|
| | | 6 | 7 | 8 |
| BSA-Control | 5 | 15.4 | 9.2 | 6.5 |
| SRIF-BSA | 5 | 17.7 | 14.8 | 11.9 |
| SRIF-IgG | 5 | 28.2 | 23.9 | 13.4 |

These results are believed to demonstrate that: (1) immunoneutralization of SRIF can provide dramatic increases in endogenous GH levels; (2) increased plasma GH levels alone can increase, rather than decrease, the fat content, unless the available metabolically-active thyroid hormone is adequate to provide increased metabolism or utilization of body fat; cf. Tables V and IX above; (3) SRIF-IgG is a superior conjugate for immunoneutralization of endogenous SRIF; and (4) ECDI is a superior coupling agent.

What is claimed is:

1. A method for lowering the extent of fat deposition in living poultry grown substantially for meat production and having normal or enhanced pituitary functions during the normal growth cycle of the poultry, which comprises:
   (a) providing growth hormone so that the poultry have an enhanced blood level of growth hormone, and
   (b) providing exogenous thyroid hormone to the living poultry during the finishing phase of the normal growth cycle of the poultry, said providing of the exogenous thyroid hormone being delayed until the poultry are at least about three weeks of age, said thyroid hormone, when compared to 3,3',5-triiodothyronine as a standard, having at least 30% of the thyroid activity and at least about 15% of the receptor-binding capability of 3,3',5-triiodo-L-thyronine.

2. A method according to claim 1, wherein said thyroid hormone is orally administered to the poultry.

3. A method according to claim 2, wherein said thyroid hormone is fed to the poultry in the finishing feed formula, in the amount ranging from approximately 10 parts per billion to about 5 parts per million, based on the weight of a daily ration of feed.

4. A method according to claim 3, wherein said amount ranges from approximately 0.1 to 2 parts per million, on the same basis.

5. A method according to claim 1, wherein the poultry are treated in accordance with the said method for at least about two weeks but for not more than the finishing phase of the growth cycle of the poultry.

6. A method according to claim 5, wherein the body fat content of the poultry is decreased as a result of said method by at least 15% by weight, compared to untreated poultry, said poultry being broiler chickens.

7. A method according to claim 1, wherein the blood level of growth hormone is increased by two to ten fold for at least 15 to 30% of each day.

8. A method according to claim 1, wherein the thyroid hormone is a metabolically-active thyroid compound of the formula

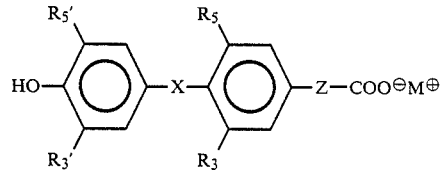

wherein
X is O, S, or CH$_2$,
Z is C$_1$–C$_4$ alkylene or amino-substituted C$_2$–C$_4$ alkylene,
M$^+$ is a physiologically acceptable cation,
R$_3$ and R$_5$ are H or iodo, at least one of them being iodo,
R$_3'$ and R$_5'$ are iodo, or hydrogen or —A—COO—M$^+$, where A is C$_2$–C$_4$ alkylene and M$^+$ is a physiologically acceptable cation, provided, that when R$_3'$, R$_5'$, R$_3$ and R$_5$ are all iodo, then Z—COO— is the residue of the anion of acetic or propionic acid;
said thyroid hormone having at least about 50% of the activity of 3,3',5-triiodo-L-thyronine.

9. A method according to claim 8, wherein X is O.

10. A method according to claim 8, wherein Z is CH$_2$; M is H; R$_3$, R$_3'$ and R$_5$ are iodo; and R$_5'$ is H.

11. A method according to claim 8, wherein Z is amino-substituted C$_2$–C$_4$ alkylene.

12. A method according to claim 11, wherein Z is amino-substituted C$_2$-alkylene in the D-configuration.

13. A method according to claim 11, wherein Z is amino-substituted C$_2$-alkylene in the L-configuration.

14. A method according to claim 11, wherein Z is amino-substituted C$_2$-alkylene in the DL-configuration.

15. A method according to claim 11, wherein R$_5'$ is H.

16. A method according to claim 1, wherein the thyroid hormone is 3,3',5-triiodo-L-thyronine, 3,3',5-triiodo-D-thyronine or 3,3',5-triiodo-DL-thyronine.

* * * * *